(12) United States Patent
Bhaskaran et al.

(10) Patent No.: US 9,254,269 B2
(45) Date of Patent: Feb. 9, 2016

(54) METHOD OF MANAGING HYPERCORTISOLEMIA, HEADACHE DISORDERS, NEUROPATHIC PAIN AND RELATED DISORDERS

(75) Inventors: Sunil Bhaskaran, Maharashtra (IN); Mohan Vishwaraman, Maharashtra (IN)

(73) Assignee: Indus Biotech Private Limited, Pune (IN)

( * ) Notice: Subject to any disclaimer, the term of this patent is extended or adjusted under 35 U.S.C. 154(b) by 56 days.

(21) Appl. No.: 13/196,625

(22) Filed: Aug. 2, 2011

(65) Prior Publication Data

US 2012/0201876 A1    Aug. 9, 2012

(30) Foreign Application Priority Data

Feb. 6, 2011 (IN) .......................... 1633/MUM/2011

(51) Int. Cl.
| | |
|---|---|
| *A01N 65/00* | (2009.01) |
| *A61K 9/48* | (2006.01) |
| *A23L 1/30* | (2006.01) |
| *A61K 9/00* | (2006.01) |
| *A61K 9/08* | (2006.01) |
| *A61K 31/704* | (2006.01) |
| *A61K 36/23* | (2006.01) |
| *A61K 47/40* | (2006.01) |
| *A61K 47/48* | (2006.01) |
| *B82Y 5/00* | (2011.01) |
| *C08B 37/00* | (2006.01) |
| *C08B 37/16* | (2006.01) |
| *C08L 5/16* | (2006.01) |
| *A61K 9/16* | (2006.01) |

(52) U.S. Cl.
CPC ............. *A61K 9/4808* (2013.01); *A23L 1/3002* (2013.01); *A61K 9/0043* (2013.01); *A61K 9/08* (2013.01); *A61K 31/704* (2013.01); *A61K 36/23* (2013.01); *A61K 47/40* (2013.01); *A61K 47/48969* (2013.01); *B82Y 5/00* (2013.01); *C08B 37/0003* (2013.01); *C08B 37/006* (2013.01); *C08B 37/0015* (2013.01); *C08L 5/16* (2013.01); *A23V 2002/00* (2013.01); *A61K 9/1652* (2013.01)

(58) Field of Classification Search
CPC combination set(s) only.
See application file for complete search history.

(56) References Cited

U.S. PATENT DOCUMENTS

| | | | | |
|---|---|---|---|---|
| 7,288,270 | B1 * | 10/2007 | Sekharam et al. ............ | 424/725 |
| 2003/0108630 | A1 * | 6/2003 | Story et al. ..................... | 424/765 |
| 2007/0207116 | A1 * | 9/2007 | Brown ......................... | 424/78.3 |
| 2008/0118583 | A1 * | 5/2008 | Olalde Rangel ............. | 424/728 |
| 2008/0194499 | A1 | 8/2008 | Bhaskaran et al. | |
| 2008/0286394 | A1 * | 11/2008 | Pushpangadan et al. ..... | 424/774 |
| 2010/0119463 | A1 * | 5/2010 | Jacobs ........................... | 424/59 |

FOREIGN PATENT DOCUMENTS

WO    WO 2005/094862    * 10/2005 ............. A61K 36/16

OTHER PUBLICATIONS

Headache, Sep. 2006; 46(8):1273-80.*
Lampl, "Antidepressants for Migraine Prophylaxis", European Neurological Journal, 2010.
Meijer et al., "Corticosterone suppresses the expression of 5-HT1A receptor mRNA in rate dentate gyrus", European Journal of Pharmacology, 266:255-261, 1994.
Saarto et al., "Antidepressants for Neuropathic pain (Review)", The Cochrane Library, Issue 11, 2010.
Moja et al., Selective serotonin re-uptake inhibitors (SSRIs) for preventing migraine and tension-type headaches, The Cochrane Library 2008, Issue 4, pp. 1-68.

* cited by examiner

*Primary Examiner* — Hasan Ahmed
(74) *Attorney, Agent, or Firm* — DLA Piper LLP (US)

(57) ABSTRACT

The present disclosure relates to treatment and management of Cushing's syndrome, Headache disorders and Neuropathic using a composition comprising asiaticoside and madecasosside optionally along with at least one excipient. The treatment can be extended to Myalgia and other related disease conditions.

6 Claims, No Drawings

METHOD OF MANAGING HYPERCORTISOLEMIA, HEADACHE DISORDERS, NEUROPATHIC PAIN AND RELATED DISORDERS

TECHNICAL FIELD

The present disclosure relates to treatment and management of Hypercortisolemia, Headache disorders and Neuropathic pain using a composition comprising asiaticoside and madecasosside optionally along with at least one excipient.

BACKGROUND AND PRIOR ART

Serotonin is a neurotransmitter involved in multiple brain functions. The receptors of serotonin commonly known as 5-hydroxy tryptamine (5-HT) receptors are extensively expressed in various sites in the body such as brain, blood vessels, heart valves, gastrointestinal tract, platelets, etc. Binding of serotonin to 5-HT receptors can induce both excitatory and inhibitory neurotransmission. There are fourteen 5-HT receptors identified. Serotonin is capable of exerting complex cardiovascular effects, including hypotension or hypertension, vasodilation or vasoconstriction, bradycardia or tachycardia etc. The action exerted by serotonin depends on the nature of the 5-HT receptor it binds along with the receptor density and sensitivity. Serotonin receptors 5-HT1A, 5-HT1B and 5-HT1D are expressed in blood vessels and central nervous system. Binding of serotonin to these receptors causes vasoconstriction in blood vessels. Drugs binding to 5-HT1B and 5-HT1D receptors are used in treatment of Migraine. However, since 5-HT1B receptors are also expressed in heart valves, long term administration of these drugs can cause cardiovalvular diseases. Similarly apart from vasoconstriction, 5-HT1A receptors are also involved in nonciceptive signal transduction. Agonist of 5-HT1A receptor can reduce pain perception to a significant level of almost 80% as compared to standard opioid drugs. Hence it is apparent that the downstream effect of serotonin varies depending on the type of 5-HT receptor it binds.

The international classification of headache disorders (2$^{nd}$ edition) describes Migraine as a neurovascular disorder characterized by severe and throbbing unilateral headache associated with anorexia, nausea, vomiting, photophobia and/or phonophobia. The most common types of Migraine are (i) Migraine with aura starting with visceral, sensory or motor symptoms followed by headache; and (ii) Migraine without aura—the headache is similar to (i) but not preceeded by aura.

Many theories exist to describe the etiology of migraine. The vascular theory states that migraine headaches result from dilatation of blood vessles which is caused by release of vasodilatatory substances like neuropeptides, neurokinins etc. It is generally accepted that this neurovascular syndrome is mainly caused by activation of trigeminovascular system. Certain brain structures that are possibly involved in Migraine have been identified as follows: the meningeal artery surrounded by mast cells in the meninges; large cerebral arteries; trigeminal nerve from meningeal arteries and cerebral arteries; and trigeminal nerve connecting the trigeminal ganglia to the trigemineal nucleus caudalis (TNC). TNC conveys the nociceptive signals to higher pain centers in the thalamus and cortex. Activation of trigemineal nerves can also cause the release of various neuropeptides including calcitonin gene related peptide at the sensory nerve endings. This causes vascular pathophysiology leading to neuro inflammation.

The serotonin theory is actually a broad statement that supports the role of increase in serotonin and 5-HIAA during the migraine attack. It has been reported that Migraine patients display an increased synthesis of serotonin in the brain as compared to normal subjects. This may lead to cortical hyperexcitability. Interestingly, it is also reported that Migraine is a low serotonin syndrome. Therefore, the involvement of serotonin in Migraine is not conclusive. Other hypotheses support the role that hormones and changes in anatomy play a role in migraine development. Hence the pathophysiology of Migraine is very complex and is not understood very clearly.

Selective serotonin reuptake inhibitors (SSRIs) are a class of compounds typically used in the treatment of depression and anxiety disorders. They increase the extracellular concentration of the neurotransmitter serotonin by inhibiting its reuptake into presynaptic neurons and increasing the serotonin available in the synaptic cleft to bind to the postsynaptic receptor. There is a misconceived notion that all SSRIs are useful drugs for Migraine. This is not true as increased levels of serotonin can bind to all 14 5-HT receptors with equal affinity and many of these are contraindicated for Migraine. Moreover, there are uncertainties about the expression of many of the 5-HT receptor proteins which are linked to other CNS conditions. For example, it is reported that 5-HT1A receptors are not synthesized in the CNS in case of high neurosteroid levels.

Lampl et al. (2010), in his article on Antidepressants for Migraine Prophylaxis published in *European Neurological Journal* has critically analyzed published data on efficacy of SSRIs for Migraine and concluded that the beneficial effects of SSRIs were equivalent to that seen in the placebo group following chronic therapy. This shows that SSRIs in general need not be useful for Migraine. Understanding the selectivity of a molecule to 5-HT receptor subtypes is crucial for determining its involvement in Migraine treatment.

Based on the definition of Migraine and its known pathophysiology, it is apparent that an ideal anti-Migraine drug should inhibit vasodilation (or cause vasoconstriction) and reduce pain perception or nociception. These two direct actions of a drug will offer potential relief from Migraine related symptoms. 5-HT1A receptors emerge as an ideal target for achieving these dual actions. Selective 5-HT1A receptor agonists have potential in offering a better anti-Migraine therapy than current standard of care for Migraine namely triptan class of drugs.

Neuropathic pain is yet another pathological pain condition characterized by persistent neuralgic pain independent of sensory stimulation along with hypersensitivity at the site of pain. It is associated with many diseases like diabetes, alcoholism, vasculitis, idiopathic polyneuropathy, spinal cord injury, cancer, stroke, HIV, degenerative neurological diseases, Guillain Barré syndrome, postherpetic neuralgia and trigeminal neuralgia. Neuropathic pain is caused by lesion or dysfunction of the peripheral or central nervous system which gives raise to symptoms of loss of sensation, paraesthesia and pain.

Neuropathic pain is not a unitary syndrome. It is a manifestation of a variety of underlying mechanisms including ectopic impulses of neuroma, changes of sodium and calcium channels in injured nerves, sympathetic activation, and deficient central inhibitory pathway are some of the pathological mechanisms.

Currently, there is no treatment which can prevent the development of Neuropathic Pain. Patients suffering from neuropathic pain do not respond to non-steroidal anti-inflammatory drugs (NSAIDs). Antidepressants and anticonvulsants are the standard of care prescribed for pain relief. However these drugs have incomplete efficacy and severe side-effects. The mechanism of action of antidepressants in treatment of Neuropathic Pain is not entirely understood. Saarto et al. (2010), in his review on antidepressants for Neuropathic Pain published in *The Cochrane Library* showed that only about one-third of patients using antidepressants have relief from Neuropathic pain and about one-fifth of the patients discontinue treatment due to severe side-effects. Based on the existing evidence of published clinical trials, SSRI drugs are not effective in treatment of Neuropathic Pain while tricyclic antidepressants are more effective in providing clinically meaningful pain relief. The activity of 5-HT1A receptor agonists in reducing pain perception may have potential in treatment of neuropathic pain.

Meijer et al. (1994, *Eur J Pharmacol.*, Vol. 266, No. 3, pp. 255-61), demonstrated that prolonged exposure of rat hippocampal cells to neurosteroids like corticosterone inhibited expression of 5-HT1A receptor mRNA. Under conditions of stress in humans, excess of neurosteroid secretion can downregulate 5-HT1A receptor expression which in turn increases the pain sensitivity. This explains Myalgia or chronic pain experienced by patients suffering from depressive disorders. Prolonged exposure of body's tissues to high levels of cortisol neurosteroid results in a disorder known as Cushing's syndrome or hypercortisolism. Cushing's syndrome can be induced by long term exogenous administration of steroid hormones like glucocortocoids, adrenocorticotropic hormone (ACTH), contraceptive pills containing estrogen hormone and other endogenous abnormalities in the body. Symptoms of Cushing's syndrome includes one or more of the following: diabetes, high blood pressure, upper body obesity, increased fat deposition around the neck, rounded face, thinning of arms and legs, severe fatigue, weak muscles etc. Irritability, anxiety, cognitive disturbances and depression are common behavioural symptoms associated with Cushing's syndrome. Treatment of Cushing's syndrome includes administration of cortisol inhibiting drugs like ketoconazole and metyrapone along with drugs for symptomatic treatment.

The present disclosure is related to treatment and management of Cushing's syndrome, Migraine, Neuropathic pain, Myalgia and related pains. These are neurological disorders that require long term management therapy. The present disclosure aims at using a botanically derived composition comprising 15-50% asiaticoside and 20-50% madecassoside optionally along with excipients, as a safe and effective treatment option for chronic administration in patients suffering from these diseases.

Bhaskaran et al. (US20080194499) discloses a composition for serotonin reuptake inhibition comprising 15-50% asiaticoside and 20-50% madecassoside. This document shows that the composition is helpful in treatment of diseases which are mediated by reduction in serotonin levels namely depression, mood elevation, gastric emptying etc., by increasing the levels for serotonin neurotransmitter. This document teaches that the composition potentiates serotonin effects by blocking reuptake of serotonin. However, there is no suggestion or clarity in the application of this composition in addressing the effects of nociceptive and neuropathic pain perception, the attenuation of vasodilation and modulating hypersecretion of neurosteroids. This application also does not teach anything about the reduction of symptoms associated with Cushing's syndrome (hypercortisolemia). This application talks about increasing the concentration of serotonin by reducing reuptake in presynaptic receptors.

STATEMENT OF DISCLOSURE

Accordingly, the present disclosure relates to a method of managing disease condition selected from a group comprising Hypercortisolemia, Headache disorder and Neuropathic pain or any combination of conditions thereof, said method comprising act of administering pharmaceutically effective amount of a composition comprising asiaticoside and madecassoside, optionally along with at least one excipient, to a subject in need thereof.

DETAILED DESCRIPTION OF THE DISCLOSURE

The present disclosure relates to a method of managing disease condition selected from a group comprising Hypercortisolemia, Headache disorder and Neuropathic pain or any combination of conditions thereof, said method comprising act of administering pharmaceutically effective amount of a composition comprising asiaticoside and madecassoside, optionally along with at least one excipient, to a subject in need thereof.

In an embodiment of the present disclosure, asiaticoside is at a concentration ranging from about 15% to about 50% and madecassoside is at a concentration ranging from about 20% to about 50%.

In another embodiment of the present disclosure, the composition is obtained from a plant *Centella Asiatica*.

In yet another embodiment of the present disclosure, the condition of the hypercortisolemia is Cushing's syndrome.

In still another embodiment of the present disclosure, the condition of the Headache disorder is selected from a group comprising Migraine, Tension headache and Cluster headache or any combination thereof.

In still another embodiment of the present disclosure, the composition is administered at dose ranging from about 1 mg/kg to about 100 mg/kg of body weight per day.

In still another embodiment of the present disclosure, the subject is an animal or human.

In still another embodiment of the present disclosure, the excipient is selected from a group comprising granulating agents, binding agents, lubricating agents, disintegrating agents, sweetening agents, glidants, anti-adherents, antistatic agents, surfactants, anti-oxidants, gums, coating agents, coloring agents, flavouring agents, coating agents, plasticizers, preservatives, suspending agents, emulsifying agents, plant cellulosic material and spheronization agents or any combination thereof.

In still another embodiment of the present disclosure, the composition is formulated into dosage forms selected from a group comprising tablet, troches, lozenges, aqueous or oily suspensions, ointment, patch, gel, lotion, dentifrice, capsule, emulsion, creams, spray, drops, dispersible powders or granules, emulsion in hard or soft gel capsules, syrups, elixirs, phytoceuticals, nutraceuticals and food stuffs or any combination thereof.

In another embodiment of the present disclosure, the composition mediates nociception, vasoconstriction and modulation of neurosteroid secretion.

In still another embodiment of the present disclosure, the composition binds selectively to 5-HT1A receptor.

In still another embodiment of the present disclosure, the composition is administered in a dosage range of 1-100 mg/kg in animals and 1-50 mg/kg in human beings per day.

In still another embodiment of the present disclosure, the process of preparation of a composition comprising asiaticoside and madecassoside, comprises the following steps:
   a. obtaining extract from the plant *Centella asiatica;*
   b. filtering and concentrating the extract;
   c. dissolving concentrated extract in a solvent to obtain a solution;
   d. treating the solution with the solvents to remove fatty substances,
   e. chlorophyll and other colorants;

f. passing treated solution through adsorbents to get a clear solution; and g. concentrating the clear solution to obtain the composition.

In still another embodiment of the present disclosure, the solvent is selected from a group comprising heterocyclic aromatic compounds, aliphatic compounds, ketones, alcohols, nitriles, esters, ether and mixtures of one or more thereof.

In still another embodiment of the present disclosure, the solvent used for extraction is preferably an aliphatic alcohol.

In still another embodiment of the present disclosure, the extraction is carried out at temperature ranging from 20° C. to 38° C. preferably at 30° C.

In still another embodiment of the present disclosure, the extraction is carried out for 6 h to 10 h preferably for 8 h.

In still another embodiment of the present disclosure, the concentration is carried out at temperature ranging from 40° C. to 50° C. preferably at 45° C.

In still another embodiment of the present disclosure, the solvent is preferably deionized water.

In still another embodiment of the present disclosure, the solvent is selected from a group comprising hexane, petroleum ether and methyl isobutyl ketone.

In still another embodiment of the present disclosure, the adsorbent is selected from a group comprising resin, charcoal, silica gel and a mixture thereof.

In still another embodiment of the present disclosure, the concentration is carried out at temperature ranging from 50° C. to 65° C.

The present disclosure also relates to manufacture a medicament comprising of asiaticoside and madecassoside optionally along with excipients for Cushing's syndrome, Migraine, Neuropathic pain and Myalgia.

In still another embodiment of the present disclosure, the excipients are selected from a group comprising granulating agents, binding agents, lubricating agents, disintegrating agents, sweetening agents, glidants, anti-adherents, anti-static agents, surfactants, anti-oxidants, gums, coating agents, coloring agents, flavouring agents, coating agents, plasticizers, preservatives, suspending agents, emulsifying agents, spheronization agents and plant derived cellulosic material.

In still another embodiment of the present disclosure, said composition is formulated into various dosage forms selected from a group comprising tablet, troches, lozenges, aqueous or oily suspensions, ointment, patch, gel, lotion, dentifrice, capsule, emulsion, creams, spray, drops, dispersible powders or granules, emulsion in hard or soft gel capsules, syrups, elixirs, liniment, ointment, skin patch, nasal spray, phytoceuticals, nutraceuticals and food stuffs.

In another embodiment of the present disclosure it is implied that the composition may comprise of cellulosic material from Centella asiatica seed in small proportions The disclosure is further elaborated with the help of following examples. However, these examples should not be construed to limit the scope of the disclosure.

EXAMPLE 1

1 kilogram of the aerial part comprising mainly the leaves and stems of the plant Centella asiatica, are taken in a clean and dry form, and pulverized to a size ensuring 100% pass through in a 20 mesh sizes hammer mill. This material was extracted with 5 litres of methyl alcohol in fixed bed counter current extractor repeatedly over a period of 10 hrs at 30° C. after 10 hrs the extract was filtered clean of all suspended matters. The clear filtrate was concentrated to a semisolid at 40 in a rotary evaporator under vacuum. To the concentrated mass 3 litres of deionised water is added to get a Homogenous liquid. The liquid was extracted by washing it twice with 2 litres of hexane and the bottom aqueous layer was separated out. The aqueous layer was again extracted twice with 1 litre of methyl isobutyl ketone. The bottom aqueous layer was separated and passed through a bed of adsorbent resin Amberlite XAD1180 (400 ml) bed maintaining a flow rate of 25 ml per minute ant the out flow was monitored for the absence of centella saponins.

The column was washed thoroughly with 5 liters in excess of Demineralised water until the washings are colorless. The adsorbents column was eluted free with ethyl alcohol until the monitoring TLC test showed absence of centello saponins in elute. The resultant elute was passed through a column comprising of 100 grams of activated charcoal and 250 grams of silica gel of the size 60 to 120 mesh. The resultant elutes were collected and the column was washed thoroughly with ethyl alcohol and all the washings combined with elute and concentrated in a vacuum distillation facility at 45-50 to get powder. This powder was dissolved in 300 ml Demineralised water to get clear solution of solid content of 20% and spray dried in a co-current indirect hot air spray dryer under following conditions: inlet temperature: 140° C. and outlet temperature: 80° C. The yield of 30 gm of pale yellow, water soluble powder with a composition of 41% asiaticoside and 36% madecassoside was obtained by the HPLC method.

EXAMPLE 2

1 kilogram of the aerial part comprising mainly the leaves and stems of the plant Centella asiatica, are taken in a clean and dry form, and pulverized to a size ensuring 100% pass through in a 20 mesh sizes hammer mill. This material was extracted with 5 liters of methyl alcohol in fixed bed counter current extractor repeatedly over a period of 8 hrs at 30° C. after 8 hrs the extract was filtered clean of all suspended matters. The clear filtrate was concentrated to a semisolid at 40 in a rotary evaporator under vacuum. To the concentrated mass 3 liters of deionised water is added to get a homogenous liquid. The liquid was extracted by washing it twice with 2 liters of hexane and the bottom aqueous layer was separated out. The aqueous layer was again extracted twice with 1 liter of methyl isobutyl ketone. The bottom aqueous layer was separated and passed through a bed of adsorbent resin Amberlite XAD1180 (400 ml) bed maintaining a flow rate of 25 ml per minute ant the out flow was monitored for the absence of centello saponins.

The column was washed thoroughly with 5 liters in excess of Demineralised water until the washings are colorless. The adsorbents column was eluted with isopropyl alcohol until the monitoring TLC test showed an absence of centello saponins in the elute. The resultant elute was passed through a column comprising of 100 grams of activated charcoal and 250 grams of silica gel of the size 60 to 120 mesh. The resultant elutes collected and the column washed thoroughly with isopropyl alcohol and all the washings combined with elute and concentrated in a vacuum distillation facility at 45 to 50 to get powder. This powder was dissolved in 300 ml Demineralised water to get clear solution of solid content of 20% and spray dried in a co-current indirect hot air spray dryer under following conditions: inlet temperature: 140° C. and outlet temperature: 80° C. The yield of 32 gm of pale yellow, water soluble powder with a composition of 39% asiaticoside and 34% madecassoside was obtained by the HPLC method.

EXAMPLE 3

10 g of 41% asicatoside and 36% madecassoide from example 1 was mixed with 1 g of 99% pure asiatocoside to arrive at a composition comprising 11 g of 46.3% asiaticoside and 32.7% madecassoside. This example demonstrates a method of arriving at desired composition range comprising 15-50% asiatocoside and 20-15% madecassoside by mixing different compositions having varied concentrations of asiaticoside and madecassoside. It is to be understood by a person skilled in the art that the composition obtained herein may be arrived at by mixing the components, asiatocoside and madecassoside, available either by extraction from plant sources or obtained by chemical synthesis of said components.

The test composition comprising 15-50% asiatocoside and 20-50% madecassoside were further tested for physiological activity in the following examples:

EXAMPLE 4

Activity of Test Composition in Olfactory Bulbectomized Rats

Bilateral olfactory bulbectomy (OBX) is an animal model of chronic depression which demonstrates the pivotal role of hypothalamic-pituitary-adrenal (HPA) axis in maintaining homeostasis. OBX induces disturbance to HPA axis and brings about behavioural and physiological changes signifying chronic depression in the animal. Following surgical recovery, OBX animals showed drastic increase in body weight. This weight gain was accompanied with other characteristic physiological changes such as increased food intake, onset of depression, elevated sodium concentration and corticosterone levels. These symptoms were found to be associated with Cushing's syndrome. It was interesting to note that OBX model mimics conditions of Cushing's syndrome.

Cushing's syndrome is associated with conditions of overweight, insulin resistance, depression, increased food intake and increased cortisol secretion. In order to study the activity of the test composition comprising 39% asiaticoside and 34% madecassoside, we used animal model of bilateral olfactory bulbectomized (OBX) rats which produces all of the above symptoms seen in Cushing's syndrome.

Procedure: Male Wistar rats were anaesthetized with Ketamine (80 mg/kg) and the olfactory bulbs were surgically aspirated by means of a blunt hypodermic needle attached to water pump without damaging the frontal lobe. Animals were allowed to recover from surgery for a period of 2 weeks. Chronic treatment with test composition was carried out for 14 days. Behavioural test was performed by placing the animals in an open field and observing the ambulation, rearing and grooming scores for a period of 5 minutes. Ambulation score was measured as mean number of squares crossed per 3 minutes. Rearing score was measured as number of rearing activity per 3 minutes. Grooming score was measured as number of grooming activity per 3 minutes. On the last day of treatment, blood was withdrawn to measure the serum corticosterone. Corticosterone is the dominant glucocorticoid found in rodents and it is the equivalent to cortisol hormone found in humans.

Results: OBX animals demonstrated 21.28% increase in body weight as compared to the normal weight gain of 7.9% seen in sham control group. The test composition significantly inhibited OBX induced increase in body weight by 12%, 16.88% and 18.56% at doses of 3, 10 and 30 mg/kg.

TABLE 1

EFFECT OF TEST COMPOSITION ON BODY WEIGHT IN OLFACTORY BULBECTOMIZED RATS (IN GRAMS)

| Time | Sham Control | OBX Control | OBX + Test composition (3 mg/kg) | OBX + Test composition (10 mg/kg) | OBX + Test composition (30 mg/kg) |
|---|---|---|---|---|---|
| Before Surgery (Day −14) | 251.2 ± 16.10 | 268.8 ± 12.60 | 273.8 ± 16.27 | 268.0 ± 13.76 | 286.6 ± 9.36 |
| After 14 days of Surgical Recovery (Day 0) | 255.4 ± 16.25 | 315.4 ± 13.46$^{\#\#\#}$ | 302.6 ± 18.25 | 299.8 ± 17.23 | 315.8 ± 9.40 |
| 7 days of Treatment | 260.0 ± 14.70 | 320.6 ± 13.03$^{\#\#\#}$ | 301.6 ± 18.79 | 287.8 ± 16.16** | 303.8 ± 9.79 |
| 10 days of Treatment | 268.0 ± 14.38 | 332.0 ± 12.19$^{\#\#\#}$ | 297.2 ± 18.04** | 283.6 ± 15.55*** | 291.8 ± 10.27*** |
| 14 days of Treatment | 273.0 ± 15.32 | 326.0 ± 13.37$^{\#\#\#}$ | 299.0 ± 17.85 | 279.8 ± 15.28*** | 294.4 ± 9.69* | n = 5; Data represented as Mean ± SEM; Data was analysed by Two-way ANOVA followed by Bonferroni Post test;
$^{\#\#\#}$p < 0.001 as compared to Sham Control group;
***P < 0.001,
**P < 0.01 and
*P < 0.05 as compared to OBX Control group.

Food intake was monitored in all test animals following 14 days of surgical recovery. Animals in the OBX control group showed 36% increase in food intake as compared to the Sham control group. Treatment with test composition at 10 and 30 mg/kg for 14 days significantly normalized food intake.

TABLE 2

EFFECT OF TEST COMPOSITION ON FOOD INTAKE IN OLFACTORY BULBECTOMIZED RATS (IN GRAMS/DAY)

| Time | Sham Control | OBX Control | OBX + Test composition (3 mg/kg) | OBX + Test composition (10 mg/kg) | OBX + Test composition (30 mg/kg) |
|---|---|---|---|---|---|
| 1 day of Treatment | 17.6 ± 0.25 | 24.0 ± 0.95$^{\#\#\#}$ | 23.1 ± 0.6 | 23.8 ± 0.97 | 17.6 ± 0.68*** |

TABLE 2-continued

EFFECT OF TEST COMPOSITION ON FOOD INTAKE IN
OLFACTORY BULBECTOMIZED RATS (IN GRAMS/DAY)

| Time | Sham Control | OBX Control | OBX + Test composition (3 mg/kg) | OBX + Test composition (10 mg/kg) | OBX + Test composition (30 mg/kg) |
|---|---|---|---|---|---|
| 7 days of Treatment | 19.6 ± 1.07 | 26.4 ± 0.93### | 23.6 ± 0.81*** | 22.8 ± 0.34*** | 17.8 ± 0.66*** |
| 14 days of Treatment | 18.8 ± 0.8 | 25.4 ± 0.51### | 25.0 ± 0.84 | 22.7 ± 0.54* | 19.8 ± 1.16* | n = 5; Data represented as Mean ± SEM; Data was analysed by Two-way ANOVA followed by Bonferroni Post test;
$P < 0.001$ as compared to Sham Control group;
***$P < 0.001$ as compared to OBX Control group.

Open field test was conducted to evaluate the locomotor activity of the animals. OBX animals showed hyperactivity confirming depression. Increased ambulation score signifying anxiety in a depressed animal exposed to a new environment. Test composition significantly reduced this hyperactivity by 30.3%, 51.2% and 64.7% at doses of 3, 10 and 30 mg/kg.

TABLE 3

EFFECT OF TEST COMPOSITION AGAINST OBX INDUCED DEPRESSION
MEASURED BY LOCOMOTOR ACTIVITY IN OPEN FIELD TEST

| Parameters | Sham Control | OBX Control | OBX + Test composition (3 mg/kg) | OBX + Test composition (10 mg/kg) | OBX + Test composition (30 mg/kg) |
|---|---|---|---|---|---|
| Ambulation Score | 32.4 ± 1.691 | 72.6 ± 6.585### | 50.6 ± 4.771*** | 35.4 ± 2.581*** | 25.6 ± 1.288*** |
| Rearing Score | 11.2 ± 1.594 | 24.4 ± 1.806### | 19.4 ± 2.561 | 18.0 ± 3.332 | 12.8 ± 1.594* |
| Grooming Score | 16.0 ± 1.817 | 22.8 ± 2.083 | 16.2 ± 1.96 | 17.6 ± 1.631 | 15.2 ± 2.010 | n = 5; Data represented as Mean ± SEM; Data was analysed by Two-way ANOVA followed by Bonferroni Post test;
$P < 0.001$ and
$P < 0.01$ as compared to Sham Control group;
***$P < 0.001$ and
*$P < 0.05$ as compared to OBX Control group.

OBX control animals showed hyper secretion of corticosterone in the blood. Animals treated with the test composition at all doses significantly reduced the corticosterone levels in the blood. OBX induced increase in serum sodium concentration which was significantly reduced by the test composition at 10 and 30 mg/kg. Reduction in blood sugar levels was also observed.

TABLE 4

EFFECT OF TEST COMPOSITION ON SERUM SODIUM AND CORTICOSTERONE
CONCENTRATIONS IN OLFACTORY BULBECTOMIZED RATS

| Parameters | Sham Control | OBX Control | OBX + Test composition (3 mg/kg) | OBX + Test composition (10 mg/kg) | OBX + Test composition (30 mg/kg) |
|---|---|---|---|---|---|
| Serum Corticosterone level (µg/ml) | 19.38 ± 0.762 | 47.18 ± 1.598### | 39.65 ± 2.955* | 28.80 ± 0.993*** | 23.62 ± 0.561*** |
| Serum Sodium Concentration (mEq/l) | 12.95 ± 0.808 | 39.59 ± 0.744### | 36.47 ± 2.547 | 16.58 ± 1.759* | 16.43 ± 1.86* | n = 5; Data represented as Mean ± SEM; Data was analysed by One-way ANOVA followed by Dunnett's Multiple Comparison test for each parameter;
$P < 0.001$ as compared to Sham Control group;
***$P < 0.001$ and
*$P < 0.05$ as compared to OBX Control group.

The study shows the efficacy of test composition in treating conditions of Cushing's syndrome namely weight gain, depression, increased food intake, cortisol hypersecretion and serum sodium increase, induced by endogenous factors demonstrated by olfactory bulbectomized rats. Hence the test composition is effective in treatment and management of Cushing's syndrome and all other conditions of hypercortisolism.

Patients suffering from depression experience sever muscular pain or Myalgia. This may be due to the increased cortisol secretion which in turn affects the expression of pain regulating 5-HT1A receptors. By reducing the corticosterone levels in OBX rats, the test composition demonstrated potential use in increasing pain tolerance and therefore efficacy in treatment and management of Myalgia and other neurological pain conditions.

EXAMPLE 5

Effect in Combination with 5-HT1A Receptor Antagonist

The activity of the test composition was evaluated by first blocking the 5-HT1A receptor with an antagonist followed by treatment with the test composition. The activity was measured in terms of immobility time of the test animals subjected to forced swim test.

Procedure: Male Swiss albino mice weighing 25-30 g were treated with antagonist of 5-HT1A receptor (NAN-190) at 1 mg/kg (p.o.) followed by administration of test composition at either 10 mg/kg (p.o.) or 30 mg/kg (p.o.). One hour after treatment, the animals were subjected to forced swim test and the immobility time was measured. A cut-off time of 360 sec was used.

Results: Animals treated only with test composition were subjected to forced swim test and a significant reduction was seen in the immobility time as compared to the normal control animals. A reduction in immobility time of about 24.87% in animals treated with 10 mg/kg of test composition and 30.14% in animals treated with 30 mg/kg of test composition were observed. Blocking of 5-HT1A receptor by an antagonist abolished this activity of the test composition indicating that action of the test composition is mediated through 5-HT1A receptor.

TABLE 5

ACTIVITY OF TEST COMPOSITION IN FORCE SWIM TEST

| | Immobility Time (sec) | % Reduction in Immobility Time |
|---|---|---|
| Normal Control | 214.3 ± 7.98 | — |
| Test Composition (10 mg/kg p.o.) | 161.0 ± 10.7[###] | 24.87 |
| Test Composition (30 mg/kg p.o.) | 149.7 ± 10.99[###] | 30.14 |
| 5-HT1A Antagonist NAN-190 (1 mg/kg p.o.) | 232.0 ± 1.63 | −8.26 |
| 5-HT1A Antagonist NAN-190 (1 mg/kg p.o.) + Test Composition (10 mg/kg p.o.) | 219.8 ± 7.66 | −2.57 |
| 5-HT1A Antagonist NAN-190 (1 mg/kg p.o.) + Test Composition (30 mg/kg p.o.) | 223.7 ± 6.76 | −4.39 | n = 6; Data represented as Mean ± SEM; Data was analyzed by One way ANOVA followed by Dunnett's multiple comparison test.
[###]$p < 0.001$ as compared to Normal Control group.

EXAMPLE 6

Effect of Test Composition in Nitroglycerine Induced Hyperalgesia in Rats

This example evaluates the potential anti-Migraine activity of the test composition by increasing pain tolerance. Nitrogylcerine induces hyperalgesia in rats by vasodilatation of cerebral arteries similar to Migraine pain in humans.

Procedure: Wistar rats of either sex weighing 200-250 g would be housed in plastic cages for at least 10 days prior to testing. Hyperalgesia was assessed using tail flick apparatus (UGO BASILE). Rats were placed in the tail flick unit in such a way that the tail occluded a slit over a photocell. Heat was applied by IR radiation and the light intensity was adjusted to give normal reaction of 8-12 seconds. A 20 seconds cut off time was used in order to prevent tissue damage. When the rat felt pain and flicked its tail, light fell on the photocell and the time was noted. After taking basal reading, rats were injected with Nitroglycerine intraperitoneally at a dose of 10 mg/kg. Fifteen minutes later, the test composition comprising 41% asiaticoside, and 36% madecassoside (30 mg/kg) or Pentazocine (20 mg/kg) was orally administered. The response latencies were measured at 30, 60, 90, 120, 180 and 240 min post treatment.

TABLE 6

RESPONSE LATENCY IN TAIL FLICK EXPERIMENT IN NITROGLYCERINE INDUCED HYPERALGESIA IN RATS

| Time period after Treatment | Normal Control | Nitroglycerine Control (10 mg/kg i.p.) | Nitroglycerine + Pentazocine (20 mg/kg p.o.) | Nitroglycerine + Test composition (30 mg/kg p.o.) |
|---|---|---|---|---|
| 0 | 9.38 ± 0.18 | 8.00 ± 0.09[###] | 8.42 ± 0.22 | 8.05 ± 0.11 |
| 30 | 8.85 ± 0.18 | 5.62 ± 0.11[###] | 15.27 ± 0.26*** | 12.72 ± 0.26*** |
| 60 | 8.03 ± 0.12 | 5.75 ± 0.12[###] | 15.23 ± 0.17*** | 12.15 ± 0.14*** |
| 90 | 8.10 ± 0.27 | 5.97 ± 0.29[###] | 15.78 ± 0.24*** | 12.88 ± 0.16*** |
| 120 | 8.33 ± 0.12 | 5.77 ± 0.19[###] | 15.50 ± 0.48*** | 12.27 ± 0.28*** |
| 180 | 9.42 ± 0.19 | 6.37 ± 0.25[###] | 15.18 ± 0.45*** | 12.77 ± 0.35*** |
| 240 | 9.05 ± 0.13 | 6.62 ± 0.24[###] | 15.03 ± 0.28* | 12.52 ± 0.39* | n = 6; Data represent Mean ± SEM; Data was analyzed by Two way ANOVA followed by Bonferroni post test.
[###]$p < 0.001$ as compared to Normal Control group;
***$p < 0.001$ as compared to Nitroglycerine Control group.

Results: The test composition significantly reversed the increased pain sensitivity induced by Nitroglycerine administration in animals. The onset of activity by the test composition was immediate. Further, the response latency in test composition group was closer to the normal animals than that of the narcotic drug Pentazocine treated group, indicating relief from pain without any sedative side effects. This study confirms that the test composition is useful in pain management and in treatment of Migraine, cluster headache, tension headache and all related headaches.

EXAMPLE 7

Effect of Test Composition in Patients Suffering from Migraine

A prospective study to assess the efficacy of the test composition against incidence of Migraine attacks was evaluated in 5 subjects diagnosed with chronic Migraine. The subjects were given capsules of the test composition at a dose of 300 mg twice daily for a period of 1 month and the efficacy of the test composition was analyzed on the basis of patient reported outcome taken at the beginning and end of the study period.

madecassoside by blending with 1.5% w/w of micro crystalline cellulose, 1% w/w of pregelatinized starch disintegrant, 0.5% w/w of crospovidone and 0.5% w/w of magnesium stearate anti-adherent. The admixed granulate was filled in the capsules.

Similar formulation of the test composition ranging from 15-50% asiatocoside and 20-50% madecassoside can be made by addition of excipient selected from a list comprising the following: granulating agents, binding agents, lubricating agents, disintegrating agents, sweetening agents, coloring agents, flavoring agents, coating agents, plasticizers, preservatives, suspending agents, emulsifying agents, spheronization agents and any combinations thereof. And the type of formulation can be selected from a group consisting of tablet, capsule, troches, lozenges, powder, syrup, solution, aerosol, suspension, dispersible powders or granules, emulsion in hard or soft gel capsules, syrups, elixirs, liniment, ointment, skin patch, phyotceuticals, nutraceuticals and food stuffs. Depending on the route of administration, different excipients/carriers may be used. Those skilled in art can choose a suitable formulation of the test composition for treatment and

TABLE 7

EFFECT OF TEST COMPOSITION IN TREATMENT OF MIGRAINE

| Symptoms | Patient 1 Before | Patient 1 After | Patient 2 Before | Patient 2 After | Patient 3 Before | Patient 3 After | Patient 4 Before | Patient 4 After | Patient 5 Before | Patient 5 After |
|---|---|---|---|---|---|---|---|---|---|---|
| Intensity of Migraine | 2 | 0 | 3 | 0 | 3 | 1 | 3 | 0 | 3 | 2 |
| Frequency of Migraine Attacks | 1 | 0 | 2 | 0 | 3 | 1 | 2 | 0 | 3 | 2 |
| Nausea/Vomiting | 0 | 0 | 0 | 0 | 3 | 3 | 3 | 0 | 2 | 2 |
| Dependence on medications for pain | 1 | 0 | 2 | 0 | 3 | 1 | 3 | 0 | 3 | 3 |
| Behavioural changes like Irritability | 0 | 0 | 3 | 0 | 3 | 3 | 2 | 1 | 2 | 2 |
| Tolerance for light, smell and noises | 2 | 1 | 3 | 0 | 3 | 2 | 3 | 1 | 2 | 2 |
| Diarrhoea, constipation or cramps | 1 | 1 | 0 | 0 | 0 | 0 | 2 | 1 | 0 | 0 |

†Scale of Severity of Migraine symptoms (0—Absence; 1—Mild; 2—Moderate; 3—Severe)

Following the initiation of administration of the test composition, subjects reported reduction in the frequency of attacks and the intensity of the Migraine headaches. Subjects also reported lower dependence on pain medications. It was further observed that there was reduction in Migraine related symptoms like irritability, reduced tolerance to light, smell, noises; nausea, vomiting etc. Hence the test composition was found to be useful to prevent and/or alleviate Migraine in human subjects.

EXAMPLE 8

Formulation of Test Composition

The capsules in Example 7 were prepared by granulation of test composition comprising 41% asiatocoside and 36% management of Hypercortisolemia (Cushing's syndrome), Migraine, Neuropathic pain, Myalgia and related pains.

EXAMPLE 9

Effect of Test Composition on Neuropathic Pain in Animals

Sciatic Nerve Crush Injury (SNCI) model of Neuropathic pain in rats was used to evaluate the therapeutic potential of test composition in treating Neuropathic pain. In SNCI model produces a partial denervation that allows for the analysis of pain behaviours evoked by stimulation of nerve's target in the hind paw.

Procedure: Male Wistar rats weighing 220-250 g were anesthetised using ketamine (80 mg/kg) and under aseptic conditions the right sciatic nerve was exposed at high thigh level. The dorsum of the nerve was freed from surrounding connective tissues and using an iris forcep the nerve was fixed in its place by pinching the epineurium on its dorsal aspect. A blunt forcep was used to crush the nerve twice for a period of 30 s with an interval of 60 s in between. Animals were allowed to recover from surgery. On day 2 after surgery the test composition comprising 41% asiaticoside and 36% madecassoside at 10, 30 and 100 mg/kg (p.o.) were administered and continued up to 30 days. Following parameters were evaluated:

a) Randall Selitto test—Increasing mechanical pressure was applied to the right hind paw and pressure at which the rat withdraws paw was noted as the nociceptive threshold pressure.

TABLE 8

PAW WITHDRAWAL PRESSURE (GRAMS) IN RANDALL SELITTO TEST

| Post Surgery Time | Normal Control | Sham Control | SNCI Control | SNCI + Test composition (10 mg/kg) | SNCI + Test composition (30 mg/kg) | SNCI + Test composition (100 mg/kg) |
|---|---|---|---|---|---|---|
| Day 0 | 267.5 ± 11.24 | 260.0 ± 10.0$^{ns}$ | 125.0 ± 6.33$^{\#\#\#}$ | 130.0 ± 7.42 | 137.5 ± 9.02 | 135.0 ± 9.49 |
| Day 7 | 282.5 ± 9.81 | 280.0 ± 10.0$^{ns}$ | 105.0 ± 3.87$^{\#\#\#}$ | 147.5 ± 11.24** | 175.0 ± 10.0*** | 187.5 ± 6.42*** |
| Day 13 | 277.5 ± 7.5 | 267.5 ± 8.14$^{ns}$ | 132.5 ± 7.16$^{\#\#\#}$ | 170.0 ± 10.72* | 205.0 ± 8.37*** | 217.5 ± 5.12*** |
| Day 21 | 285.0 ± 5.48 | 285.0 ± 7.75$^{ns}$ | 145.0 ± 3.16$^{\#\#\#}$ | 200.0 ± 9.22* | 225.0 ± 3.87* | 272.5 ± 4.61*** | n = 6; Data represent Mean ± SEM; Data was analyzed by Two way ANOVA followed by Bonferroni post test.
$^{ns}$not significant as compared to Normal Control group;
$^{\#\#\#}$P < 0.001 as compared to Sham Control group;
***P < 0.001,
**P < 0.01 and
*P < 0.05 as compared to SNCI Control group.

b) Von Frey filament—Mechano-tactile allodynia was assessed by applying force using rigid nylon filaments of 1 mm diameter to the mid-plantar surface of right hind paw. A brisk withdrawal of the right hind limb was considered a positive response and the force at which the rat withdraws its paw was noted.

TABLE 9

PAW WITHDRAWAL FORCE (GRAMS) IN VON FREY FILAMENT TEST

| Post Surgery Time | Normal Control | Sham Control | SNCI Control | SNCI + Test composition (10 mg/kg) | SNCI + Test composition (30 mg/kg) | SNCI + Test composition (100 mg/kg) |
|---|---|---|---|---|---|---|
| Day 0 | 100.60 ± 1.694 | 97.65 ± 3.134$^{ns}$ | 36.85 ± 1.912$^{\#\#\#}$ | 40.15 ± 3.524 | 40.05 ± 2.964 | 46.683 ± 4.002 |
| Day 7 | 105.72 ± 1.634 | 101.38 ± 2.64$^{ns}$ | 54.9 ± 3.12$^{\#\#\#}$ | 61.73 ± 4.205 | 61.68 ± 3.54* | 75.03 ± 2.441*** |
| Day 13 | 109.07 ± 1.02 | 105.18 ± 1.17$^{ns}$ | 64.03 ± 1.98$^{\#\#\#}$ | 70.4 ± 3.21 | 75.57 ± 2.05* | 80.1 ± 1.92*** |
| Day 21 | 107.07 ± 1.49 | 106.52 ± 1.75$^{ns}$ | 66.22 ± 1.64$^{\#\#\#}$ | 75.18 ± 0.89 | 81.73 ± 1.43* | 86.98 ± 1.43* | n = 6; Data represent Mean ± SEM; Data was analyzed by Two way ANOVA followed by Bonferroni post test.
$^{ns}$not significant as compared to Normal Control group;
$^{\#\#\#}$P < 0.001 as compared to Sham Control group;
***P < 0.001 and
*P < 0.05 as compared to SNCI Control group.

c) Tail immersion test—Spinal thermal sensitivity was assessed by immersing the terminal part of the tail of the rat in cold temperature ranging from 0-4° C. and measuring the duration of tail withdrawal reflex. A cut-off time of 15 seconds was used.

TABLE 10

RESPONSE LATENCY (SECONDS) IN TAIL IMMERSION TEST

| Post Surgery Time | Normal Control | Sham Control | SNCI Control | SNCI + Test composition (10 mg/kg) | SNCI + Test composition (30 mg/kg) | SNCI + Test composition (100 mg/kg) |
|---|---|---|---|---|---|---|
| Day 0 | 10.17 ± 0.65 | 9.83 ± 0.83$^{ns}$ | 2.97 ± 0.1$^{\#\#\#}$ | 2.9 ± 0.09 | 3.0 ± 0.07 | 9.33 ± 0.71 |
| Day 7 | 11.5 ± 0.56 | 10.5 ± 0.85$^{ns}$ | 2.7 ± 0.09$^{\#\#\#}$ | 3.4 ± 0.11 | 3.6 ± 0.07 | 3.93 ± 0.11 |

TABLE 10-continued

RESPONSE LATENCY (SECONDS) IN TAIL IMMERSION TEST

| Post Surgery Time | Normal Control | Sham Control | SNCI Control | SNCI + Test composition (10 mg/kg) | SNCI + Test composition (30 mg/kg) | SNCI + Test composition (100 mg/kg) |
|---|---|---|---|---|---|---|
| Day 13 | 10.0 ± 0.52 | 10.5 ± 0.67$^{ns}$ | 3.67 ± 0.08$^{\#\#\#}$ | 3.95 ± 0.09 | 4.35 ± 0.16 | 6.15 ± 0.16*** |
| Day 21 | 10.88 ± 0.57 | 11.17 ± 0.54$^{ns}$ | 4.25 ± 0.13$^{\#\#\#}$ | 4.6 ± 0.13 | 5.08 ± 0.22 | 6.85 ± 0.16*** | n = 6; Data represent Mean ± SEM; Data was analyzed by Two way ANOVA followed by Bonferroni post test.
$^{ns}$not significant as compared to Normal Control group;
$^{\#\#\#}$P < 0.001 as compared to Sham Control group;
***P < 0.001 as compared to SNCI Control group.

d) Motor coordination test—Motor coordination was evaluated using a rota-rod device. Rats were placed for 1 min on the rotating rod. The time taken for the falling from the roller was recorded as the grip strength.

TABLE 11

GRIP STRENGTH (SECONDS) IN MOTOR COORDINATION TEST

| Post Surgery Time | Normal Control | Sham Control | SNCI Control | SNCI + Test composition (10 mg/kg) | SNCI + Test composition (30 mg/kg) | SNCI + Test composition (100 mg/kg) |
|---|---|---|---|---|---|---|
| Day 0 | 42.167 ± 1.28 | 40.83 ± 1.33$^{ns}$ | 22.83 ± 0.54$^{\#\#\#}$ | 22.5 ± 0.43 | 23.0 ± 0.37 | 24.67 ± 0.76 |
| Day 7 | 42.17 ± 0.6 | 42.0 ± 1.21$^{ns}$ | 21.5 ± 0.43$^{\#\#\#}$ | 25.0 ± 0.58 | 26.0 ± 0.37** | 27.67 ± 0.56*** |
| Day 13 | 41.5 ± 0.96 | 44.17 ± 1.19$^{ns}$ | 26.42 ± 0.42$^{\#\#\#}$ | 27.5 ± 0.43 | 30.5 ± 0.67* | 33.5 ± 1.06*** |
| Day 21 | 43.5 ± 0.96 | 44.5 ± 1.34$^{ns}$ | 28.83 ± 0.4$^{\#\#\#}$ | 30.67 ± 0.42 | 33.5 ± 1.06 | 37.67 ± 0.92* | n = 6; Data represent Mean ± SEM; Data was analyzed by Two way ANOVA followed by Bonferroni post test.
$^{ns}$not significant as compared to Normal Control group;
$^{\#\#\#}$P < 0.001 as compared to Sham Control group;
***P < 0.001,
**P < 0.01 and
*P < 0.05 as compared to SNCI Control group.

Results: The test composition significantly reduced neuropathic pain symptoms induced by sciatic nerve crush injury in rats. Significant reduction in hyperalgesia, allodynia and thermal sensitivity of the injured limb was seen on chronic treatment with test composition. Motor coordination of the injured animal was also normalized by the test composition as seen from the rota-rod test. Hence the test composition is useful in treating Neuropathic pain and its symptoms on chronic use.

EXAMPLE 10
Effect of Test Composition in Patients Suffering from Neuropathic Pain A prospective study to assess the efficacy of the test composition in managing Neuropathic pain was evaluated in 3 patients over 50 years of age suffering from diabetes for 3-5 years. The patients were given capsules of test composition as formulated in example 8, at a dose of 300 mg twice daily for a period of 2 months and the efficacy of the test composition was analyzed on the basis of patient reported outcome taken at the beginning and end of the study period.

TABLE 12

EFFECT OF TEST COMPOSITION IN TREATMENT OF NEUROPATHIC PAIN

| | Patient Recorded Outcome† | | | | | |
|---|---|---|---|---|---|---|
| | Patient 1 | | Patient 2 | | Patient 3 | |
| Symptoms | Before | After | Before | After | Before | After |
| Sudden Pain attacks | 5 | 4 | 5 | 4 | 4 | 2 |
| Burning sensation in area of pain | 4 | 3 | 4 | 4 | 4 | 3 |
| Tingling or Pricking sensation in area of pain | 4 | 3 | 4 | 3 | 4 | 3 |
| Sensation of numbness in area of pain | 4 | 2 | 2 | 2 | 4 | 4 |
| Pain triggered by applying slight pressure with a finger in area of pain | 0 | 0 | 4 | 3 | 3 | 2 |
| Pain triggered due to cold/heat water bath in area of pain | 0 | 0 | 4 | 3 | 3 | 3 |

TABLE 12-continued

EFFECT OF TEST COMPOSITION IN
TREATMENT OF NEUROPATHIC PAIN

| | Patient Recorded Outcome† | | | | | |
|---|---|---|---|---|---|---|
| | Patient 1 | | Patient 2 | | Patient 3 | |
| Symptoms | Before | After | Before | After | Before | After |
| Pain triggered due to light exposure | 0 | 0 | 0 | 0 | 3 | 2 |

†Scale of Severity of Neuropathic Pain (0—Absence; 1—Hardly Noticed; 2—Mild; 3—Moderate; 4—Strong; 5—Very Strong)

Following the initiation of administration of the test composition, the subjects reported reduction in the frequency of sudden pain attacks. Decrease in the intensity of burning sensation, tingling, numbness and pain caused by triggers such as touch, hot/cold water bath, light exposure etc., were reported. The test composition was found to be useful in managing Neuropathic pain in human subjects.

EXAMPLE 11

Nasal Spray Formulation of Test Composition 55 mg of test composition comprising 46.8% asiaticoside and 31.8% madecassoside was dissolved in 140 ml of normal saline (0.09% w/v of NaCl). To this 10 mg of benzalkonium chloride was added and stirred for 1 hr. This mixture was sterilized and filtered through 0.4 micron filter and filled in nasal spray bottles. One shot of the nasal spray delivers 140 μl of the formulation which is equivalent to 55 μg of test composition.

EXAMPLE 12

Effect of Nasal Spray in Nitroglycerine Induced Hyperalgesia in Rats

This example evaluates the potential activity of the test composition formulated as nasal spray. Nitrogylcerine induces hyperalgesia in rats by vasodilatation of cerebral arteries similar to Migraine pain in humans.

Procedure: Wistar rats of either sex weighing 200-250 g would be housed in plastic cages for at least 10 days prior to testing. Hyperalgesia was assessed using tail flick apparatus (UGO BASILE). Rats were placed in the tail flick unit in such a way that the tail occluded a slit over a photocell. Heat was applied by IR radiation and the light intensity was adjusted to give normal reaction of 8-12 seconds. A 20 seconds cut off time was used in order to prevent tissue damage. When the rat felt pain and flicked its tail, light fell on the photocell and the time was noted. After taking basal reading, rats were injected with Nitroglycerine intraperitoneally at a dose of 10 mg/kg. Fifteen minutes later, the test composition formulated in Example 11 was sprayed into the nasal cavity. The response latencies were measured at 30, 60, 90, 120, 180 and 240 min post treatment.

TABLE 13

EFFECT OF NASAL SPRAY FORMULATION
OF TEST COMPOSITION IN NITROGLYCERINE
INDUCED HYPERALGESIA IN RATS

| Time period after Treatment | Normal Control | Nitroglycerine Control (10 mg/kg i.p.) | Nitroglycerine + Nasal Spray (110 μg/kg) |
|---|---|---|---|
| 0 | 8.8 ± 0.17 | 8.22 ± 0.17### | 8.08 ± 0.32 |
| 30 | 8.7 ± 0.19 | 6.55 ± 0.17### | 9.8 ± 0.67*** |
| 60 | 8.65 ± 0.22 | 6.12 ± 0.20### | 10.77 ± 0.41*** |
| 90 | 8.35 ± 0.12 | 5.82 ± 0.17### | 10.62 ± 0.52*** |
| 120 | 8.42 ± 0.23 | 6.00 ± 0.22### | 10.57 ± 0.67*** |
| 240 | 8.42 ± 0.28 | 5.88 ± 0.29### | 10.67 ± 0.74*** | n = 6; Data represent Mean ± SEM; Data was analyzed by Two way ANOVA followed by Bonferroni post test.
$P < 0.001$ as compared to Normal Control group;
***$P < 0.001$ as compared to Nitroglycerine Control group.

Results: The test composition formulated as nasal spray significantly reversed pain sensitivity induced by Nitroglycerine. The onset of activity was immediate similar to oral treatment shown in Example 6. The dose required to achieve this effect using nasal spray was also significantly low, demonstrating enhanced delivery of the test composition through the nasal route. This study confirms that the test composition formulated as nasal spray is safe and efficacious in pain management. Hence the test composition formulated as nasal spray is useful in the treatment and management of hypercortisolemia (Cushing's syndrome), Migraine, Neuropathic pain, Myalgia and related pains.

EXAMPLE 13

Cyclodextrin Complexing of Test Composition

This example shows that the test composition can be complexed with cyclodextrins namely $\alpha$, $\beta$ and $\gamma$-cyclodextrins to enhance the stability of the test composition against gastric or intestinal fluids.

200 ml of demineralized water is taken and 50 grams of $\beta$-cyclodextrin is added to this under agitation at 80-85° C. to get a clear solution. To this 40 grams of test composition comprising 46.8% asiaticoside and 31.8% madecassoside is slowly added in portions over a period of 1 hr under agitation at 85° C. The complete dissolution of the mixture by formation of a clear solution is crucial, following which the solution is maintained at 85-90° C. for 3 hrs under agitation. After 3 hrs, the solution is allowed to cool slowly at room temperature and the solution is kept under agitation for another 8 hrs. The solution is filtered and vacuum dried at 75° C. to constant weight. Yield is 73 grams. 100 mg of this complex dissolves in 7 ml of demineralized water.

We claim:

1. A method of treating a disease condition selected from the group consisting of hypercortisolemia, headache disorder and neuropathic pain or any combination of conditions thereof, comprising administering a pharmaceutically effective amount of a composition consisting of asiaticoside, madecassoside, and at least one excipient, to a subject in need thereof, wherein the asiaticoside is at a concentration ranging from about 15% to 50% and the madecassoside is at a concentration ranging from about 20% to 50%, and wherein the excipient is selected from the group consisting of granulating agents, binding agents, lubricating agents, disintegrating agents, sweetening agents, glidants, anti-adherents, anti-static agents, surfactants, gums, coating agents, coloring agents, flavouring agents, plasticizers, preservatives, suspending agents, emulsifying agents, plant cellulosic material and spheronization agents or any combination thereof.

2. The method of claim 1, wherein the composition is obtained from a plant *Centella asiatica*.

3. The method of claim 1, wherein the condition of the headache disorder is selected from a group comprising migraine, tension headache and cluster headache or any combination thereof.

4. The method of claim 1, wherein the composition is administered at dose ranging from about 1 mg/kg to 100 mg/kg of body weight per day.

5. The method of claim 1, wherein the subject is a non-human animal or a human.

6. The method of claim 1, wherein the composition is formulated into dosage forms selected from the group consisting of tablets, troches, lozenges, aqueous or oily suspensions, ointments, patch, gels, lotions, dentifrices, capsules, emulsions, creams, spray, drops, dispersible powders or granules, emulsion in hard or soft gel capsules, syrups, elixirs, phytoceuticals, nutraceuticals and food stuffs or any combination thereof.

* * * * *